United States Patent [19]

Krause

[11] Patent Number: 5,745,647

[45] Date of Patent: Apr. 28, 1998

[54] METHOD AND APPARATUS FOR AUTOMATICALLY CONTROLLING AND SCALING MOTOR VELOCITY

[75] Inventor: Kenneth W. Krause, Sandown, N.H.

[73] Assignee: Smith & Nephew, Inc., Andover, Mass.

[21] Appl. No.: 529,191

[22] Filed: Sep. 15, 1995

[51] Int. Cl.$^6$ ........................................................ H02P 7/18
[52] U.S. Cl. .................... 388/827; 388/937; 318/568.11; 318/568.18; 318/628; 318/624; 901/9
[58] Field of Search ........................... 388/827, 937; 318/568.11, 568.16, 568.18, 568.22, 628, 624; 901/9

[56] References Cited

U.S. PATENT DOCUMENTS

| | | | |
|---|---|---|---|
| 4,059,786 | 11/1977 | Jones et al. | 318/17 |
| 4,375,964 | 3/1983 | Knopp et al. | 433/29 |
| 4,387,325 | 6/1983 | Klimo | 318/17 |
| 4,634,941 | 1/1987 | Klimo | 318/139 |
| 5,134,600 | 7/1992 | Oliver et al. | 901/9 X |
| 5,307,271 | 4/1994 | Everett, Jr. et al. | 318/568.11 X |
| 5,340,953 | 8/1994 | Krebs et al. | 200/86.5 |
| 5,347,204 | 9/1994 | Gregory et al. | 318/568.11 X |

*Primary Examiner*—Karen Masih
*Attorney, Agent, or Firm*—Fish & Richardson P.C.

[57] ABSTRACT

A method and apparatus automatically associate a sensed mechanical parameter to a range of motor velocity for controlling the rotational velocity of a motor driving a medical instrument. The method and apparatus sense or measure the mechanical parameter whose value, controlled by a human operator, through for example, a footpad, can be measured and converted to a digital signal. The method and apparatus, in response to the measured sensed mechanical parameter, automatically scale the range of parameter values to a new range of motor velocity values thereby adjusting, to the mechanical displacement (force or distance) with which the user is most comfortable. The transformation also provides deadband values around the minimum and maximum motor velocities so that maximum motor velocity is not "chased" and minimum motor velocity is not sensitive to small perturbations due to thermal effects and other events which may affect the mechanical sensor output.

30 Claims, 3 Drawing Sheets

METHOD AND APPARATUS FOR AUTOMATICALLY CONTROLLING AND SCALING MOTOR VELOCITY

The invention relates to control methods and apparatus for controlling motor velocity for driving medical devices, and more particularly, to a method and apparatus for effecting automatic control and scaling of motor velocity in a system for driving surgical cutting instruments.

BACKGROUND OF THE INVENTION

In surgical processes which employ motor driven drills, saws, and other generally rotary or oscillatory tools, it is common to use a mechanically responsive sensor, such as a footpad, to control the rotational speed of the drive motor. In typical use, if the footpad uses positional sensing to control the speed of the drive motor, different operators, having different sensitivity to the footpad position, can find that the motor velocity varies unexpectedly depending upon the last adjustments to footpad operation and accordingly manual readjustment of the footpad sensor response may be required to acceptably control the rotational speed of the drive motor for different users.

Footpads or footswitches which use force sensing technology, as opposed to displacement, possess a different variable quality which varies from person to person. That is, the actuation pressure and the span pressure can vary significantly from person to person. Existing methods for tailoring a specific footpad or footswitch to an operator use, like the displacement sensitive footpads, manual adjustments or buttons.

It is accordingly an object of the invention to correlate the pressure applied to a footpad or footswitch to the maximum rotational velocity of a driven motor for driving a surgical instrument without requiring manual adjustments such as the need to manually control speed varying buttons or switches. Other objects of the invention are a low cost, reliable, automatic method and apparatus for adapting automatically to different operators to control a motor driven surgical instrument.

SUMMARY OF THE INVENTION

The invention relates to a method and apparatus for automatically associating a sensed mechanical parameter to a transformed value in a range of motor velocity values for controlling the rotational velocity of a motor driving a medical instrument. The mechanical parameter has a value which is controlled by a human operator, and is typically set using, for example, a foot pad. The method features the steps of measuring the value of the sensed mechanical parameter controlled by the operator, automatically determining a user controlled maximum parameter value from measurements of the sensed parameter, and scaling the measured values of the sensed parameter to the range of values of the motor velocity wherein a minimum value of the sensed parameter corresponds to no rotation of the motor and the determined maximum value of the sensed parameter corresponds to a maximum rotational value of the motor.

In specific aspects, the method of the invention further features the steps of determining whether a current measured parameter has at least a minimum value and, if the value is not greater than the minimum value, maintaining the motor at a zero velocity. If the value is greater than the minimum value, the velocity of the motor is set to a value corresponding to the current measured parameter value. The actual motor velocity is set in accordance with the scaled range of values.

In other particular embodiments of the invention, the scaling step operates to provide a substantially linear transformation from the range of parameter values to the range of motor velocity values, and the method can further feature the steps of defining a maximum deadband range of values bracketing the determined maximum determined parameter value and setting the velocity of the motor to the motor maximum velocity value whenever the scaled value of the mechanical parameter is within the bracketed deadband range of values. The method can also provide for stopping the rotational motion of the motor when the measured parameter value is below a determined lower limit.

The apparatus of the invention features a sensor for measuring the value of the sensed mechanical parameter controlled by the operator, a controller for automatically determining a user controlled maximum parameter value from measurements of the sensed parameter, and wherein the controller scales the measured values of the sensed parameter to a range of motor velocity values so that a minimum value of the parameter corresponds to no rotation of the motor and the determined maximum value of the parameter corresponds to a maximum rotational velocity of the motor.

In specific embodiments of the apparatus, according to the invention, a controller determines whether a current measured parameter value has at least a minimum value and if the value is greater than the minimum value, the controller sets the motor velocity to a value corresponding to the measured parameter value using the scaled range of values. The maximum parameter value is set to a higher value if the current measured parameter value exceeds the previously set maximum parameter value; and if that occurs, the controller provides for rescaling the new range of possible parameter values to the range of motor velocity values. Preferably, the scaling is performed by a substantially linear-transformation scaler.

In yet other aspects of the invention, the controller can provide a deadband range of values bracketing the determined maximum parameter value so that the controller sets the velocity of the motor to the motor maximum velocity value whenever the scaled value of the mechanical parameter is within the bracketed deadband range of values. The apparatus can also feature a braking circuit for stopping rotational motion of the motor when the measured value is below a determined lower limit.

BRIEF DESCRIPTION OF THE DRAWINGS

Other objects features and advantages of the invention will be apparent from the following description taken together with the drawings in which.

DESCRIPTION OF THE PREFERRED EMBODIMENT

Figure 1:
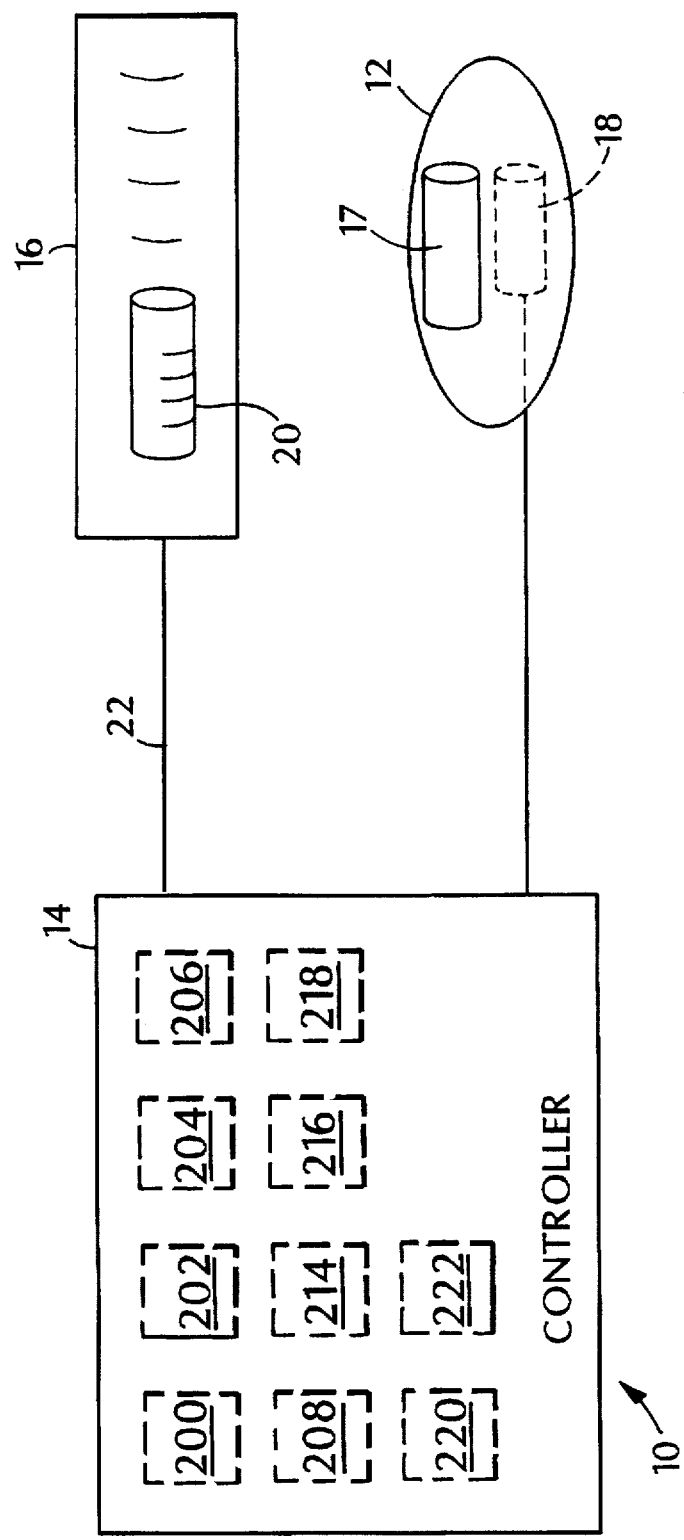
FIG. 1 is a general block diagram illustrating the operation of the invention.

Referring to FIG. 1, in a typical system 10, according to the invention, there is a footpad 12, a controller 14, and a driven surgical instrument 16. The footpad 12 typically has a pressure sensitive activation surface 17 to which a pressure sensor 18 shown in phantom in FIG. 1 is sensitive. The output of the pressure sensor represents the amount of force applied to surface 17 and thus represents a mechanical parameter in response to which controller 14 determines the rotational velocity of a motor 20 within and driving surgical instrument 16.

The controller 14, for example a microprocessor driven device such as Phillips microcontroller model No. 87-C-552, receives the output of pressure sensor 18 and converts it to a digital value (an eight bit value between 0 and 255 in the illustrated embodiment). In response to the received digital values from pressure sensor 18, the controller scales a range of pressures corresponding to the forces measured by the pressure sensor 18 to a range of 0 to 255 (a full 8 bit range) and then translates that scaled range to a motor drive signal which is available over lines 22 to the motor 20. The motor 20 is operatively connected to drive a medical instrument such as a saw, drill, etc. for use by the surgeon during an operation.

Figure 2:
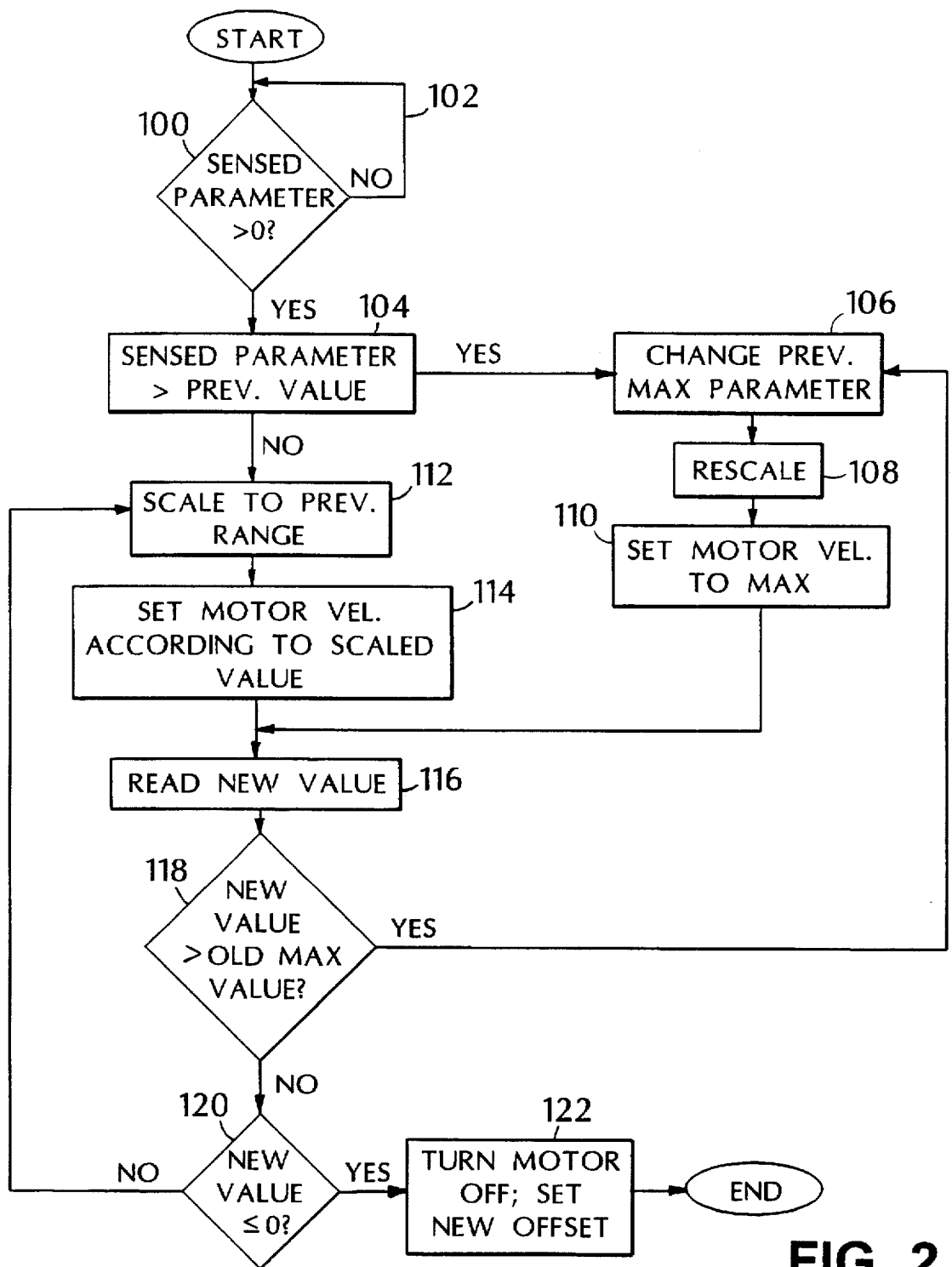
FIG. 2 is a flow chart illustrating operation of the controller in accordance with a preferred embodiment of the invention.

In operation, referring to FIG. 2, the controller first reads the sensed parameter and determines, at 100, whether its value corresponds to a pressure greater than zero (that is, whether the sensor has been activated). In order to accommodate thermal and other error inducing effects, an offset value is subtracted from the pressure reading to create, effectively, a deadband region around zero pressure. If the offset modified pressure reading is not greater than zero (the minimum parameter value), then the system loops back on itself, through path 102, waiting for activation of the apparatus. At this point in time, the maximum value of the parameter has been set to zero and the system is ready to automatically adapt to the applied pressure.

Once pressure is applied to the sensor 18, the offset modified sensor output parameter takes a value greater than zero. If the sensor parameter is greater than the previously sensed maximum value, at 104, then the previously sensed maximum parameter value is changed at 106, the values are rescaled at 108, and the motor velocity is accordingly set to its maximum value at 110. If the sensed offset modified parameter value is not greater than the previously determined maximum value, then the offset modified sensed value is converted to a motor velocity digital value, by scaling it in accordance with the previously determined range of parameter values, at 112, and the motor velocity is set according to the scaled value (the motor velocity parameter) at 114. Thereafter, a next value of the sensor output is read and sampled at 116.

If the new offset modified sensor value is greater than the old maximum sensor value, as determined at 118, than the old maximum value is changed at 106. Otherwise, the new value is checked to see whether it is greater than zero at 120. If it is not greater than zero, the motor is turned off at 122 in accordance with a predetermined process. Otherwise, the value is scaled according to the previously determined range of values at 112. If the motor is turned off, the process terminates and awaits a new sensed parameter at which time the maximum value will have again been reset to zero. In a preferred particular embodiment of the invention, the maximum value is immediately reset to zero and a new offset value is determined when the motor is off. Further, to accommodate thermal and other effects, which may cause drift, a new offset value is determined approximately every one-half second when the motor is off.

Figure 3:
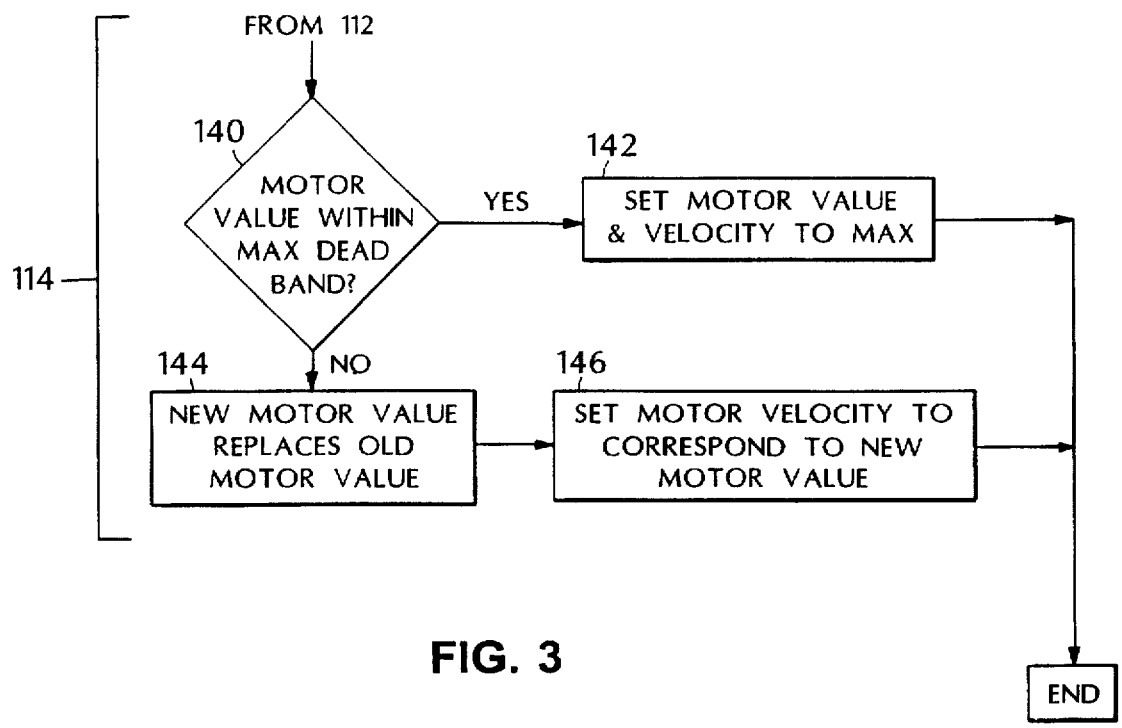
FIG. 3 is a more detailed flow chart of a section of FIG. 2.

Referring now to FIG. 3, the motor velocity is set according to the scaled digital value by first checking whether the scaled motor velocity digital value is within a deadband which extends below the maximum motor velocity (or maximum scaled parameter value of 255). This is indicated at 140. If the value is within the deadband, the motor velocity is set to a maximum motor velocity at 142. This allows a small variation (20% in the illustrated embodiment) in the pressure applied to the footpad around the maximum pressure value, without having the motor velocity change (fall) precipitously, for example, during an operation, even though the sensed footpedal or footpad pressure may vary slightly. It also eliminates the need to chase the maximum motor velocity value. If the motor value is not within the deadband, the new motor value replaces the old motor value at 144 and the new motor value is used to control and set the motor velocity, at 146, by setting the motor velocity equal to a value corresponding to the new motor parameter digital value. Thereafter, the set motor velocity step terminates; and the system and method pass to the next step to read the next value at block 116.

In operation, the process of scaling, or rescaling, by controller 14, works according to the following principle. (The attached software appendix describes this method of operation in greater detail, and provides a working software program written in microprocessor assembly language.)

First, an offset modified variable speed index (R3) having a value of 0–255 (in other words 8 bit accuracy) is tested for an "off" (zero) value. The offset modified, variable speed index is determined by subtracting the offset value from the measured values. The offset is determined to be that value, which, when subtracted from the current "off" measured value (that is, no pressure on the footpad) corresponds to negative 0.098 volts, in the illustrated embodiment. If the offset modified variable speed index, is less than zero, then the "maximum" variable (R6) indicating the maximum value of the mechanical parameter, is reset to zero. If the offset modified variable speed index is greater than zero, indicating that the footswitch is determined to be in an "on" state, the variable speed index (R3) is compared with the maximum value previously determined by the controller, that is the current value of R6, and if the newly read value of the variable speed index R3 is greater than the current value of the maximum value (R6), then R6 is updated with the value of R3. This automatically detects, therefore, the maximum pressure applied during this "on" cycle and it is this value which is used to scale the lesser values of the variable speed index R3 up to a full scale eight bit value (of 255). In this manner, also, the full scale index becomes the motor velocity value index so that the motor velocity controlling parameter always has a range of values between zero and 255.

With enough microprocessor power, a conventional method for determining the velocity digital value is to multiply R3 times 255 (using a 16 bit multiply) and dividing the result by R6 to get an 8 bit result x. Thus, the value of x is determined by the result of Equation 1 which reads as follows:

$$x/255 = R3/R6 \quad \text{(Eq. 1)}$$

This takes approximately, in the microprocessor system described above, 250 microseconds. In a second, preferred, alternate method of operation, an approximate value of x can be determined as follows.

In accordance with the preferred embodiment of the invention, an approximately linear transformation is obtained, at a substantial savings in calculation time, by first dividing 255 by the maximum sensed parameter value (R6). The fractional portion (255 modulus R6) is saved and the integer value of the division is multiplied by the value of the current measured parameter (R3). The product of the current parameter value (R3), times the integer value of the previous division+1, times the saved fractional value (255 modulus R6) is then divided by 256 (an 8 bit shift in the microprocessor) to yield an 8 bit result. The 8 bit result is then added to the previous multiplication of R3 and the integer value. This produces a value which approximates the value of x identified above in Equation 1 and using the microprocessor system described above takes about 25 microseconds.

The method described above provides a "landing pad" so that a user does not chase the maximum pressure value by, for example, pushing the footpad pedal "through the floor". In accordance with the method, the digital motor parameter "x" is increased by adding approximately 20 percent to the previous calculation of "x". In the microprocessor, this is performed by multiplying x by 51 and adding the upper 8 bits of the 16 bit product to x. This value is also protected from overflow and the result is used by the system as the motor variable speed index for controlling and determining motor velocity. "x" is thus an 8 bit parameter and has a range of zero to 255.

Thus, in accordance with the invention, and as described above, two provisions are made to better control motor velocity. First, a deadband of values is placed below the maximum value of the variable speed motor index, so that small changes in the variable speed index from the maximum value will not have any effect upon the actual motor velocity. Thus, in a preferred embodiment, the deadband is such that if any scaled value from 230 through and including 255 results in a maximum motor output speed. The effect is to allow an approximately 20 percent variation in foot pressure before motor speed will be impacted. Thus the user does not have to chase the maximum pressure "through the floor". This allows an appropriate upper landing pad for the system thereby enabling better user control over the driven surgical instrument.

In the second aspect, a deadband is effectively provided to effect a "landing pad" or "soft landing" around zero motor velocity by subtracting an offset from the measured pressure parameter. In the illustrated embodiment, the offset is selected so that a zero pressure on the footpad corresponds to a negative 0.098 volts.

It is important to recognize that while the invention has been described primarily in terms of the computer program of the Software Appendix, the controller 14 can, of course, also be implemented in hardware or in a combination hardware and software. When implemented in hardware, that is, using the equivalent hardware components to the Software Appendix program, the controller 14 would include, with appropriate interconnection as is well known in the art, a resetting circuit 200, a rescaling circuit 202, a transforming circuit 204, a comparer 206, a circuit for increasing the scaled measured value 208, arithmetic elements including at least one multiplier 214, at least one adder 216, at least one divider 218, a subtractor 220, and circuitry 222 for periodically determining the offset value. In addition, the controller can implement the transformation $S=S_m \cdot X_c/X_m$ where $X_c$ is a current measured parameter value, S is the scaled parameter value, $X_m$ is the maximum parameter value, and $X_c$ is the maximum allowable scaled value. This equation, as will be apparent, is completely equivalent to equation one noted above Addition, subtractions, and other modifications of the described embodiments will be apparent to one of ordinary skill in the field and are within the scope of the following claims.

Software Appendix

```
status
        acall   device
        mov     a,r7                        ; indicates if footswitch is on
        jz      off                         ; footswitch was off
        mov     a,#offset
        add     a,mask
        mov     r0,a                        ; pointer to active offset
        acall   adc
        subb    a,@r0                       ; subtract offset
        jnc     on                          ; pedal is still on
        mov     calctr,#255
        mov     calctr+1,#7
off
        inc     calctr
        mov     a,calctr
        jnz     off0
        inc     calctr+1
        mov     a,calctr+1
        cjne    a,#8,off0                   ; about 1/2 second
        mov     calctr+1,#0
        acall   calibrate                   ; reset counter and calibrate
off0    mov     r0,#offset
        mov     mask,#0
off1    acall   adc
        clr     c
        subb    a,@r0                       ; subtract offset
        jnc     on                          ; pedal turned on if >=0
        inc     r0
        inc     mask
        cjne    r0,#offset+3,off1           ; loop until done
off3    clr     a                           ; all three pedals are off so reset
        mov     r7,a
        mov     mask,a
```

Software Appendix

```
                mov     max,a
                mov     target,a
digital
                mov     a,p3
                cpl     a
                anl     a,#18h          ; read speed buttons
                orl     a,r7            ; combine with pedal status
                cjne    a,stat,state    ; goto new state if different
                ret
on
                mov     r2,a            ; save adc value
                cjne    a,max,$+3       ; compare with max
                jc      on1
                mov     max,a           ; save if new or same max
on1             mov     a,#255          ; autosensitivity
                mov     b,max
                div     ab              ; a = int(255 / max)
                mov     r3,a            ; b = 255 mod max
                inc     a
                mul     ab
                mov     b,r2
                mul     ab              ; b = [r2 * (int+1) * mod] / 256
                mov     a,r3
                mov     r3,b
                mov     b,r2
                mul     ab              ; a = r2 * int
                add     a,r3            ; a = [r2 * int] + [r2 * (int+1) * mod] / 256
                jc      on2
                mov     r2,a
                mov     b,#51
                mul     ab
                mov     a,r2            ; add 20% hysteresis
                add     a,b
                jnc     on3
on2             mov     a,#255
on3             mov     target,a
                mov     a,mask
                inc     a               ; indicates pedal status
                rl      a
                mov     r7,a
                ajmp    digital
; subroutine reads 8 bits from adc channel mask adc             mov     adcn,mask       ; prepare to read adc channel
                orl     adcn,#8
                mov     a,adcn
                jnb     acc.4,$-2
                anl     adcn,#0EFh      ; reset interrupt flag
                mov     a,adch          ; read high byte
                cpl     a
                ret
; subroutine calculates new offsets calibrate
                mov     r0,#offset
                mov     mask,#0         ; channel 0
cal             acall   adc             ; start adc
                add     a,#5            ; .098 volt guard band
                jnc     call
                mov     a,#255          ; clamp at maximum
call            mov     @r0,a           ; new offset for channel
                inc     mask            ; next channel
                inc     r0
                cjne    r0,#offset+3,cal
                ret
```

What is claimed is:

1. A method for automatically associating a sensed mechanical parameter to a transformed value in a range of motor velocity values for controlling the rotational velocity of a motor driving a medical instrument, said mechanical parameter having a value controlled by a human operator, comprising the steps of measuring a value of the sensed mechanical parameter controlled by said operator, automatically determining a user controlled maximum parameter value from measurements of said sensed parameter, and scaling the measured values of said sensed parameter to said range of motor velocity values wherein a minimum

9 value of said parameter corresponds to no rotation of said motor and said determined maximum value of said parameter corresponds to a maximum rotational velocity of said motor.

2. The method of claim 1 further comprising the steps of determining whether a current measured parameter has at least a minimum value, and if said value is no greater than said minimum value, maintaining said motor at a zero velocity, and if said value is greater than said minimum value, setting said motor velocity to a value corresponding to said current measured parameter value modified according to said scaled range of values.

3. The method of claim 2 further comprising the steps of resetting said maximum parameter value, if said current measured parameter value exceeds the value of the current maximum parameter value, and rescaling said range of parameter values to said range of motor velocity.

4. The method of claim 1 wherein said scaling step comprises the step of transforming a current measured parameter value $X_c$ to a scaled parameter value S when the maximum parameter value is $X_m$ according to the transformation $S=S_m \cdot X_c/X_m$ where $S_m$ is the maximum allowable scaled value.

5. The method of claim 1 wherein said scaling step is substantially a linear transformation.

6. The method of claim 1 wherein said determining step further comprises the steps of comparing a current value of said mechanical parameter with said determined maximum parameter value, and resetting said maximum parameter value to said current parameter value when said current value is greater than said maximum parameter value.

7. The method of claim 1 further comprising the steps of defining a maximum range deadband range of values bracketing the determined maximum parameter value, and setting the velocity of the motor to said motor maximum velocity value whenever the scaled measured value of said mechanical parameter is within said bracketed deadband range of values.

8. The method of claim 7 wherein said defining step comprises the step of increasing the scaled measured value by a fixed percentage value after scaling and prior to determining motor velocity.

9. The method of claim 8 wherein said increasing step comprises the steps of multiplying an eight bit scaled measured value by a selected integer factor to obtain a sixteen bit result having an upper eight bits and a lower eight bits, and adding the upper eight bits of said sixteen bit multiplication product to said scaled measured value.

10. The method of claim 1 wherein said scaling step comprises the steps of dividing $S_m$, a maximum scaled motor velocity value, by the determined maximum parameter value for finding an integer portion I and a fractional portion F, multiplying the integer portion by a current measured parameter value to yield $M_1$, multiplying the current measured parameter value times the integer value incremented by one, times the fractional portion to yield a product, and dividing the product by 256 to yield an eight bit result, and adding the eight bit result to $M_1$, to yield a value which approximates the scaled measured value.

11. The method of claim 1 further comprising the step of subtracting an offset value from said measured value prior to said determining and scaling steps.

12. The method of claim 11 further comprising the step of periodically determining said offset value when said motor is off.

13. The method of claim 1 further comprising the steps of defining a stop deadband range of values bracketing a zero value of said measured value of said mechanical parameter, and stopping rotational motion of said motor when said mechanical parameter value has a value within said stop deadband range of values.

14. The method of claim 1 further comprising the step of resetting said maximum parameter values to a minimum value whenever the measured parameter is within a stop deadband range of values.

15. A method for automatically associating a sensed mechanical parameter to a transformed value in a range of motor velocity values for controlling the rotational velocity of a motor driving a medical instrument, said mechanical parameter having a value controlled by a human operator, comprising the steps of measuring a value of the sensed mechanical parameter controlled by said operator, automatically determining a user controlled maximum parameter value from measurements of said sensed parameter, said determining step comprising the steps of comparing a current value of said mechanical parameter with said determined maximum parameter value, and resetting said maximum parameter value to said current parameter value when said current value is greater than said maximum parameter value, scaling the measured values of said sensed parameter to said range of motor velocity values wherein a minimum value of said parameter corresponds to no rotation of said motor and said determined maximum value of said parameter corresponds to a maximum rotational velocity of said motor, determining whether a current measured parameter has at least a minimum value, if said value is no greater than said minimum value, maintaining said motor at a zero velocity, if said value is greater than said minimum value, setting said motor velocity to a value corresponding to said current measured parameter value modified according to said scaled range of values, defining a maximum range deadband range of values bracketing the determined maximum parameter value, setting the velocity of the motor to said motor maximum velocity value whenever the scaled measured value of said mechanical parameter is within said bracketed deadband range of values, defining a stop deadband range of values bracketing a zero value of said measured value of said mechanical parameter, stopping rotational motion of said motor when said mechanical parameter value has a value within said stop deadband range of values, and resetting said maximum parameter values to a minimum value whenever the measured parameter is with a stop deadband range of values.

16. Apparatus for automatically associating a sensed mechanical parameter to a transformed value in a range of motor velocity values for controlling the rotational velocity of a motor driving a medical instrument, said mechanical parameter having a value controlled by a human operator, said apparatus comprising a sensor for measuring a value of the sensed mechanical parameter controlled by said operator, a controller for automatically determining a user controlled maximum parameter value from measurements of said sensed parameter, and said controller scaling the measured values of said sensed parameter to said range of motor velocity values wherein a minimum value of said parameter corresponds to no rotation of said motor and said determined maximum value of said parameter corresponds to a maximum rotational velocity of said motor.

17. The apparatus of claim 16 further comprising said controller determining whether a current measured parameter has at least a minimum value, and if said value is no greater than said minimum value, said controller maintaining said motor at a zero velocity, and if said value is greater than said minimum value, said controller setting said motor velocity to a value corresponding to said current measured parameter value modified using said scaled range of values.

18. The apparatus of claim 17 said controller further comprising means for resetting said maximum parameter value if said current measured parameter value exceeds the current maximum parameter value, and means for rescaling said range of parameter values to said range of motor velocity.

19. The apparatus of claim 16 wherein said controller comprises means for transforming a current measured parameter value $X_c$ to a scaled parameter value S when the maximum parameter value is $X_m$ according to the transformation $S=S_m \cdot X_c/X_m$ where $S_m$ is the maximum allowable scaled value.

20. The apparatus of claim 16 wherein said controller employs a substantially linear transformation scaler.

21. The apparatus of claim 16 wherein said determining means further comprises a comparer for comparing a current value of said mechanical parameter with said determined maximum parameter value, and means for resetting said maximum parameter value to said current parameter value when said current value is greater than said maximum parameter value.

22. The apparatus of claim 16 further comprising said controller defining a maximum range deadband range of values bracketing the determined maximum parameter value, and said controller sets the velocity of the motor to said motor maximum velocity value whenever the scaled measured value of said mechanical parameter is within said bracketed deadband range of values.

23. The apparatus of claim 22 wherein said controller comprises means for increasing the scaled measured value by a fixed percentage value after scaling and prior to determining motor velocity.

24. The apparatus of claim 23 wherein said increasing means comprises a multiplier for multiplying an eight bit scaled measured value by a selected integer factor to obtain a sixteen bit result, and an adder for adding the upper eight bits of said sixteen bit multiplication product to said scaled measured value.

25. The apparatus of claim 16 wherein said controller comprises a divider for dividing $S_m$, the maximum scaled motor velocity value, by the determined maximum parameter value for finding an integer portion I and a fractional portion F, a multiplier for multiplying the integer portion by the current measured parameter value to yield $M_1$, a second multiplier for multiplying the current measured parameter value times the integer value incremented by one, times the fractional value, and dividing the product by 256 to yield an eight bit result, and a second adder for adding the eight bit result to $M_1$, to yield a value which approximates the scaled measured value.

26. The apparatus of claim 16 further comprising a subtractor for subtracting an offset value from said measured value prior to operation of said controller determining and scaling operations.

27. The apparatus of claim 26 further comprising means for periodically determining said offset value when said motor is off.

28. The apparatus of claim 16 further comprising said controller defining a stop deadband range of values bracketing the zero value of said measured value of said mechanical parameter, and a braking circuit for stopping rotational motion of said motor when said mechanical parameter value has a value within said stop deadband range of values.

29. The apparatus of claim 16 further comprising means for resetting said maximum parameter values to a minimum value whenever the measured parameter is with a stop deadband range of values.

30. Apparatus for automatically associating a sensed mechanical parameter to a transformed value in a range of motor velocity values for controlling the rotational velocity of a motor driving a medical instrument, said mechanical parameter having a value controlled by a human operator, comprising a sensor for measuring the value of the sensed mechanical parameter controlled by said operator, a controller for automatically determining a user controlled maximum parameter value from measurements of said sensed parameter, said controller scaling the measured values of said sensed parameter to said range of motor velocity values wherein a minimum value of said parameter corresponds to no rotation of said motor and said determined maximum value of said parameter corresponds to a maximum rotational velocity of said motor, said controller determining whether a current measured parameter has at least a minimum value, if said value is no greater than said minimum value, maintaining said motor at a zero velocity, and if said value is greater than said minimum value, setting said motor velocity to a value corresponding to said current measured parameter value modified according to said scaled range of values, said controller resetting said maximum parameter value, if said current measured parameter value exceeds the value of the current maximum parameter value, said controller rescaling said range of parameter values to said range of motor velocity, said controller defining a maximum range deadband range of values bracketing the determined maximum parameter value, said controller setting the velocity of the motor to said motor maximum velocity value whenever the scaled measured value of said mechanical parameter is within said bracketed deadband range of values, said controller defining a stop deadband range of values bracketing the zero value of said measured value of said mechanical parameter, stopping rotational motion of said motor when said mechanical parameter value has a value within said stop deadband range of values, and said controller resetting said maximum parameter values to a minimum value whenever the measured parameter is within a stop deadband range of values.

* * * * *